(12) United States Patent
Chin (10) Patent No.: US 6,547,796 B1
(45) Date of Patent: Apr. 15, 2003

(54) MIDFACE MOBILIZING INSTRUMENT

(75) Inventor: Martin Chin, Alameda, CA (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 0 days.

(21) Appl. No.: 09/575,099

(22) Filed: May 19, 2000

Related U.S. Application Data (60) Provisional application No. 60/135,328, filed on May 20, 1999.

(51) Int. Cl.$^7$ .............................................. A61B 17/66
(52) U.S. Cl. ............................ 606/105; 606/87; 606/90
(58) Field of Search ............................ 606/53, 86, 87, 606/90, 105, 205–209; 600/184, 201, 210, 217

(56) References Cited

U.S. PATENT DOCUMENTS

| | | | | |
|---|---|---|---|---|
| 2,075,534 A | * | 3/1937 | McCormack | 606/219 |
| 2,291,413 A | * | 7/1942 | Siebrandt | 606/103 |
| 3,960,147 A | * | 6/1976 | Murray | 606/75 |
| 5,603,723 A | * | 2/1997 | Aranyi et al. | 606/205 |
| 5,810,812 A | * | 9/1998 | Chin | 606/53 |
| 6,168,601 B1 | * | 1/2001 | Martini | 606/90 |

* cited by examiner

Primary Examiner—Kevin Shaver
Assistant Examiner—Michael B. Priddy
(74) Attorney, Agent, or Firm—Harness, Dickey & Pierce, P.L.C.

(57) ABSTRACT

An instrument for mobilizing the midface bones of a human skull in which at least a partial osteotomy between the midface bones and the skull has been performed. A first member includes a dentition engaging portion for engaging the dental arch of the maxilla. A second member includes a nasal engaging portion for engaging the nasal floor of the nasal cavity. An adjustable member is connected to the first member and to the second member and is adjustable to draw the first and second members toward each other so that the first member can be drawn against the dental arch and the second member can be drawn against the nasal floor. A lever is connected to at least one of the first and second members. The lever is disposed anteriorly of the forehead and extends in a superior-inferior direction relative to the skull when the first and second members are engaged with the dental arch and nasal floor, respectively. Simultaneously pulling the lever anteriorly and pushing the forehead posteriorly breaks the midface bones free from the skull.

20 Claims, 8 Drawing Sheets

MIDFACE MOBILIZING INSTRUMENT

CROSS-REFERENCE TO RELATED APPLICATIONS

This application claims the benefit of U.S. Provisional Application No. 60/135,328, filed May 20,1999.

FIELD OF THE INVENTION

The present invention relates generally to instruments for craniomaxillofacial surgery, and more particularly to surgical instruments for mobilizing the bones of the midface in preparation for advancement of the midface with gradual distraction.

BACKGROUND OF THE INVENTION

Hypoplasia of the midface associated with syndromic craniosynostosis remains a primary challenge to craniomaxillofacial surgeons. Respiration, vision, speech, and esthetics are all affected by impairment of midfacial development. Compromise of function related to midface hypoplasia represents a significant disability. The surgical challenge is to correct the combined skeletal and soft tissue deficiency. Tessier pioneered subcranial and transcranial osteotomies to address the deficiency of craniofacial development. The Le Fort III osteotomy with internal fixation and bone grafting became a standard treatment for these deformities. Despite remarkable improvement in form and function as a result of these procedures, significant deformity often persisted. The magnitude of correction achieved with these procedures often fell short of the ideal anatomical objective. As a result, management of these patients often required repeated procedures to increase the correction. When full correction of the midface was not possible, compensating osteotomies of the maxilla and mandible have been performed to improve the facial balance and dental occlusion. Repeating the procedure or combining it with a Le Fort I maxillary advancement was a common strategy to overcome the limitation in achievable advancement. Even though osteotomies fully separate the midfacial skeleton, the investing soft tissue deficiency limits the effectiveness of conventional osteotomies with intraoperative fragment protraction. Distraction osteogenesis has made it possible to overcome many of the limitations imposed by the deficiency in soft tissue. Distraction can simultaneously enlarge the skeleton and soft tissue. This approach is essential for optimal reconstruction of these disorders.

Even though distraction substantially improves the potential correction of retruded midfaces at the Le Fort III level, the osteotomy and mobilization of the fragment remains a major surgery with significant morbidity. Penetrating the cranial vault during osteotomy, fragment mobilization, or placement of fixation/distraction devices is a known risk. Laceration of the brain by penetration of the cranial vault may result in neurological deficit or death. Intracranial penetration may also occur when reflecting coronal flaps in a field previously treated by forehead advancement. Conventional Le Fort III technique involves complete osteotomy under direct vision followed by fragment mobilization using Kiley-Rowe disimpacting forceps. The purchase of the disimpacting forceps to the Le Fort III fragment is often insecure. The nasal floor contour may not conform to the prongs of the forcep beaks. The oral purchase is on the palate placing the beaks on the mucosa and toward the midline. Transmission of force through the forceps into the Le Fort III fragment is inefficient. Because the efficiency of force generation to mobilize the Le Fort III fragment is poor, a complete osteotomy is essential. Even small areas of incomplete osteotomy will prevent fragment mobilization. Injury to the soft tissue including the eyes and brain may occur if the osteotomy site is over-instrumented. Generating force with the instrument requires counter-traction of the head and is awkward. This is because the vector of force necessary to mobilize the midface with disimpacting forceps is not aligned with the vector of primary resistance.

It would be desirable to provide an improved instrument for mobilizing the Le Fort III midface fragment that alleviates the above-described disadvantages of the Kiley-Rowe disimpacting forceps. Such an improved instrument is provided by the present invention.

SUMMARY OF THE INVENTION

In accordance with the present invention, an instrument is provided that is modular and arranged to be assembled in situ. An acrylic splint, preferably custom made for the patient, attaches rigidly to the instrument and positively engages the dental arch of the maxilla. Alternatively, a general use resilient platform may be used to engage the dental arch. Two nasal floor prongs clamp the device in place rigidly. A primary lever extends in the superior-inferior direction in front of the forehead. A secondary lever extends in the medial-lateral direction in from of the dental arch. When mobilization is performed, reciprocal traction is exerted between the forehead and the primary lever. The resultant force on the head and neck is low because the two force vectors are in opposite directions. Torsional force can be exerted via the secondary lever. Controlled force of large magnitude may be exerted on the midface.

Advantages of the present invention include the following. A complete osteotomy is not necessary to obtain a satisfactory mobilization if limited osteotomies in the critical structural buttresses are established. This eliminates the need for complete orbital floor osteotomies and requires limited nasal-frontal osteotomy. Pterygoid plate separation is generally not necessary. Many of the hazardous sites for osteotomy become unnecessary. Transoral access can provide adequate mobilization for major Le Fort III level movements. Protection of the nasal lacrimal system, however, is compromised with limited access. Prophylactic intubation with silicone tubing may be necessary to prevent obstruction of lacrimal drainage. The invention allows for midface mobilization with less bone cutting than with prior art devices and methods. Therefore, the risk of penetrating the cranial vault and injuring the brain is reduced. The orientation of the primary lever in the superior-inferior direction allows reciprocal application of force which decreases the amount of energy needed to stabilize the head during mobilization and reduces the risk of neck injury. The wider stabilization of the device to the dental arch as compared to the middle of the palate with Rowe-Kiley forceps allows greater force to be applied in a torsion manner. This allows mobilization of the zygoma with the midface unit and decreases the risk of an aberrant fracture along the Le Fort II line.

According to one aspect of the present invention, a method of mobilizing the midface bones of a human skull includes the steps of performing a partial osteotomy between the midface bones and the skull and breaking the midface bones free of the skull.

According to another aspect of the present invention, an instrument for mobilizing the midface bones of a human skull includes a grasping member for grasping the midface bones. A lever has a first portion connected in cantilever fashion to the grasping member and has a second portion displaced from the grasping member in a superior-inferior direction relative to the skull. Manually displacing the second portion of the lever in an anterior-posterior direction relative to the skull breaks the midface bones free from the skull.

It is an object of the present invention to provide an improved instrument for effecting mobilization of the midface bones of a skull.

It is a further object of the present invention to provide an improved method of mobilizing the midface bones of a skull.

Other objects and advantages of the present invention will be apparent from the description below of the preferred embodiments and methods for practicing the invention, made with reference to the drawings.

DETAILED DESCRIPTION OF THE PREFERRED EMBODIMENTS

Figure 1:
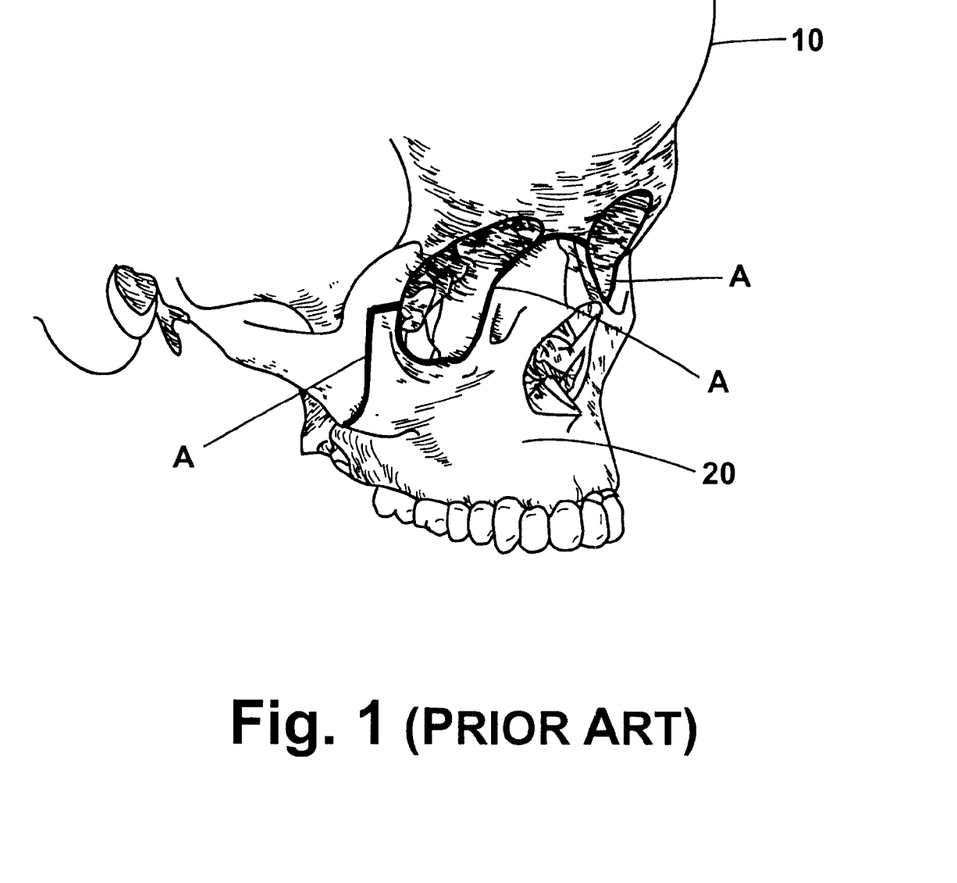
FIG. 1 is a perspective view of a skull on which the location of the Le Forte III osteotomy is marked, in accordance with the surgical technique known in the prior art.

Referring to FIG. 1, a skull 10 is illustrated on which the locations of the Le Fort III osteotomies are marked by the dark line A, as known in the prior art surgical method for Le Fort III advancement of the midface. Performing osteotomies at the locations marked by line A permits mobilization and advancement of the Le Fort III midface fraction 20 relative to skull 10.

Figure 2:
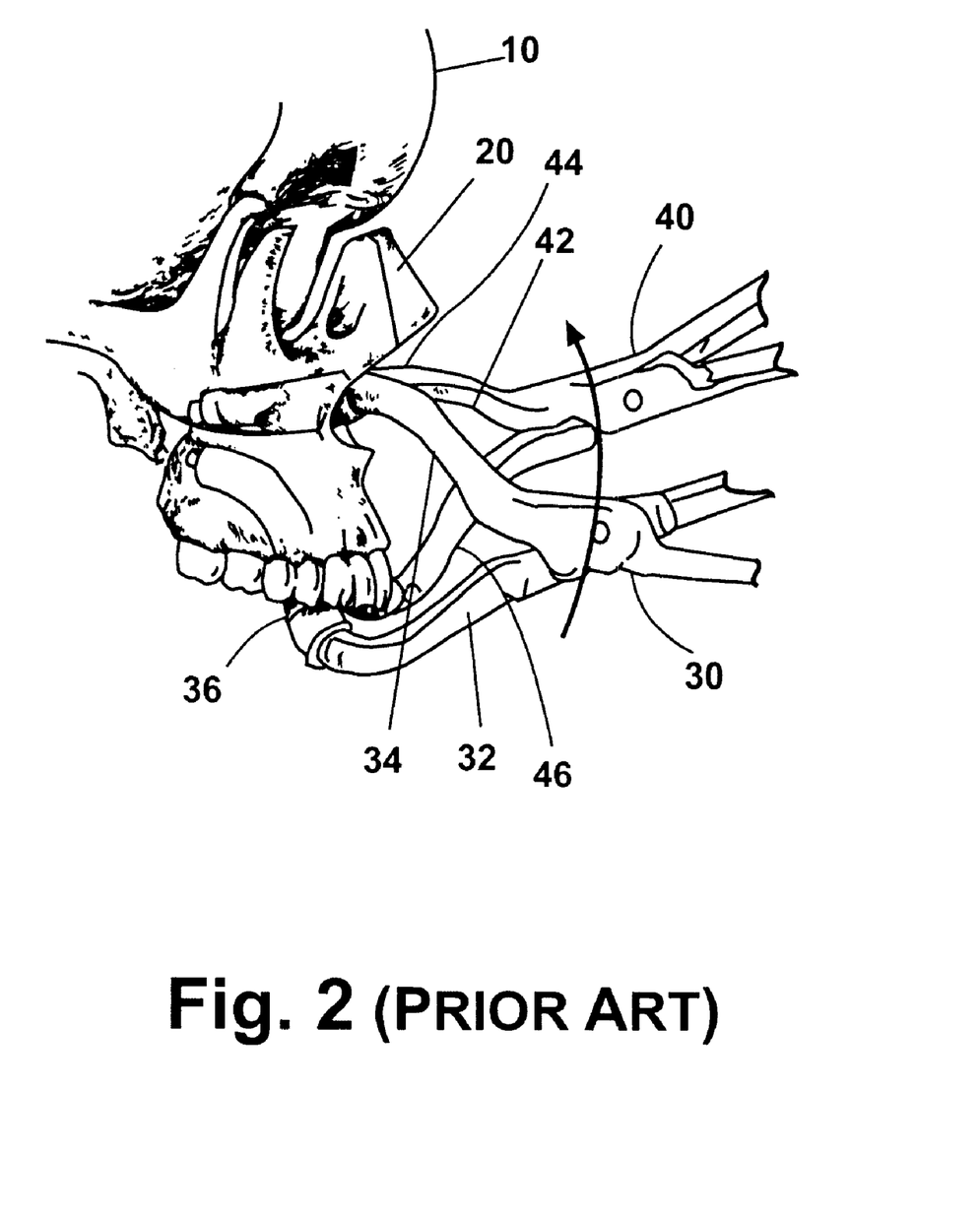
FIG. 2 is a perspective view of a skull showing the prior art surgical technique of mobilizing the midface, after performing the Le Forte III osteotomies, using Kiley-Rowe disimpacting forceps.

Referring to FIG. 2, mobilization of the Le Fort III midface fraction 20 is shown using a pair of Rowe-Kiley disimpacting forceps 30 and 40, in accordance with the surgical method known in the prior art. Each pair of forceps includes respective beaks 32 and 42. Each beak 32 and 42 includes an upper prong 34 and 44, respectively, and a lower prong 36 and 46, respectively. Upper prongs 34 and 44 are configured to be received within the nasal cavity, and lower prongs 36 and 46 are configured to be received within the oral cavity. Upper prongs 34 and 44 are configured to gain purchase on the nasal floor. Lower prongs 36 and 46 are curved to conform generally to the palate and gain purchase thereon. Conventional Le Fort III technique using Kiley-Rowe disimpacting forceps involves complete osteotomy under direct vision followed by fragment mobilization. The purchase of the disimpacting forceps to the Le Fort III fragment is often insecure. The nasal floor contour may not conform to the prongs 34, 44 of the forcep beaks 32, 42. The oral purchase is on the palate placing the prongs 36, 46 on the mucosa and toward the midline. Transmission of force through the forceps 30, 40 into the Le Fort III fragment 20 is inefficient. Because the efficiency of force generation to mobilize the Le Fort III fragment is poor, a complete osteotomy is essential. Even small areas of incomplete osteotomy will prevent fragment mobilization.

Figure 3:
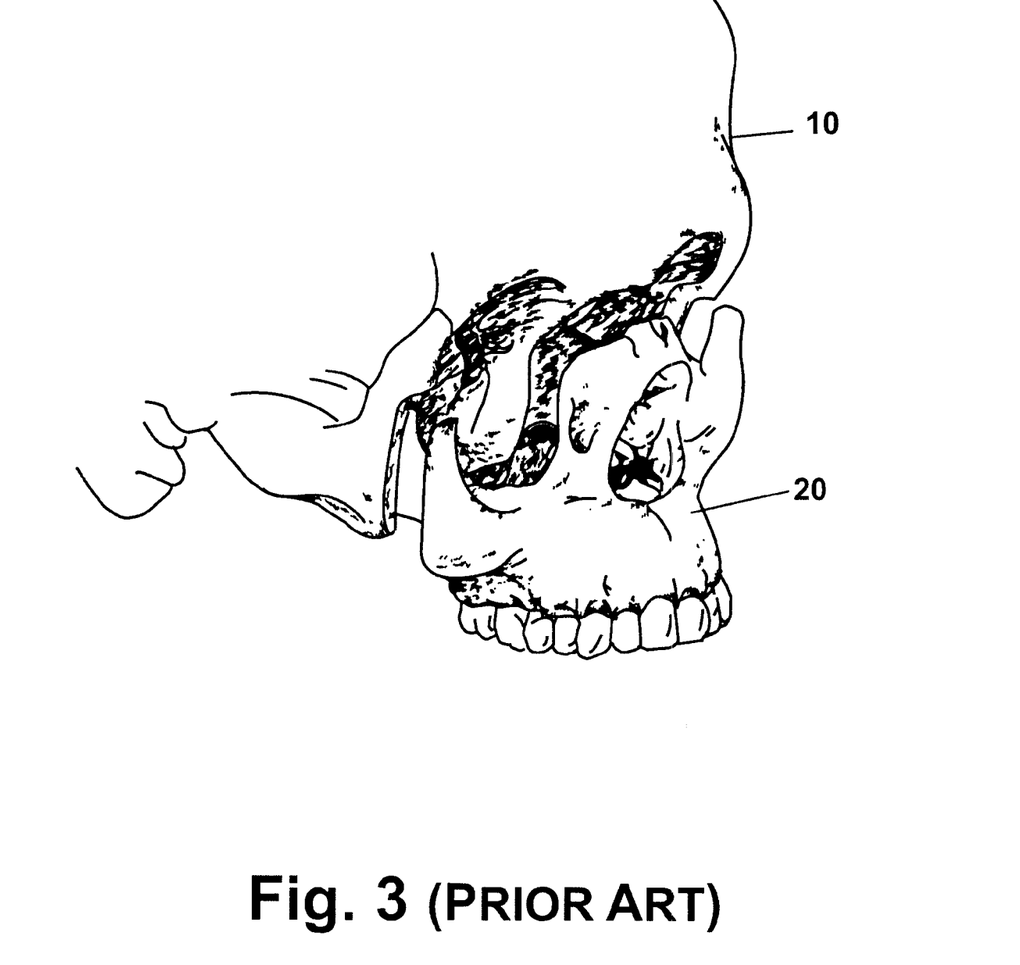
FIG. 3 is a perspective view of a skull showing the Le Forte III midface fragment separated from the skull after performing the Le Forte III osteotomies and using the disimpacting forceps.

Referring to FIG. 3, skull 10 and Le Fort III midface fragment 20 are shown following completion of the Le Fort III osteotomies and before implantation of distraction devices, in accordance with the prior art surgical method involving complete osteotomies.

Figure 4:
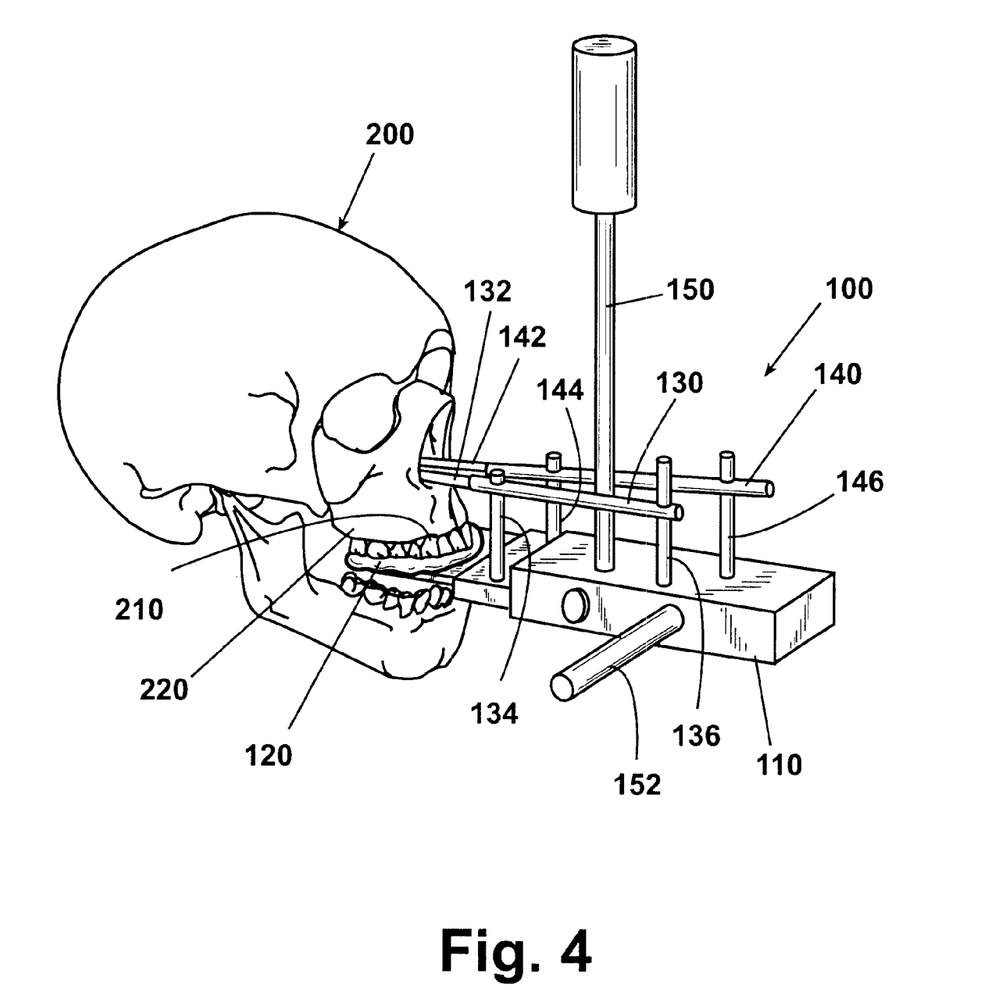
FIG. 4 is a perspective view of a skull and of an embodiment of an instrument according to the present invention, showing the placement of the instrument relative to the skull during use.

Referring to FIG. 4, a midface mobilization instrument 100, constructed in accordance with the present invention, is shown emplaced relative to skull 200. Instrument 100 includes as its principle components a plate 110, a splint 120 secured to plate 110 and engaging the dental arch 210 of the maxilla 220 of skull 200, a pair of retention rods 130 and 140 having respective nasal extension prongs 132 and 142, a primary lever 150 affixed to plate 110 and cantilevered therefrom and extending in the superior-inferior direction, and a secondary lever 152 affixed to plate 110 and cantilevered therefrom and extending in the medial-lateral direction. Screws 134 and 136, and screws 144 and 146, connect retention rods 130 and 140, respectively, to plate 110 and provide for adjustment of the distance and angle between rods 130, 140 and plate 110.

Figure 5:
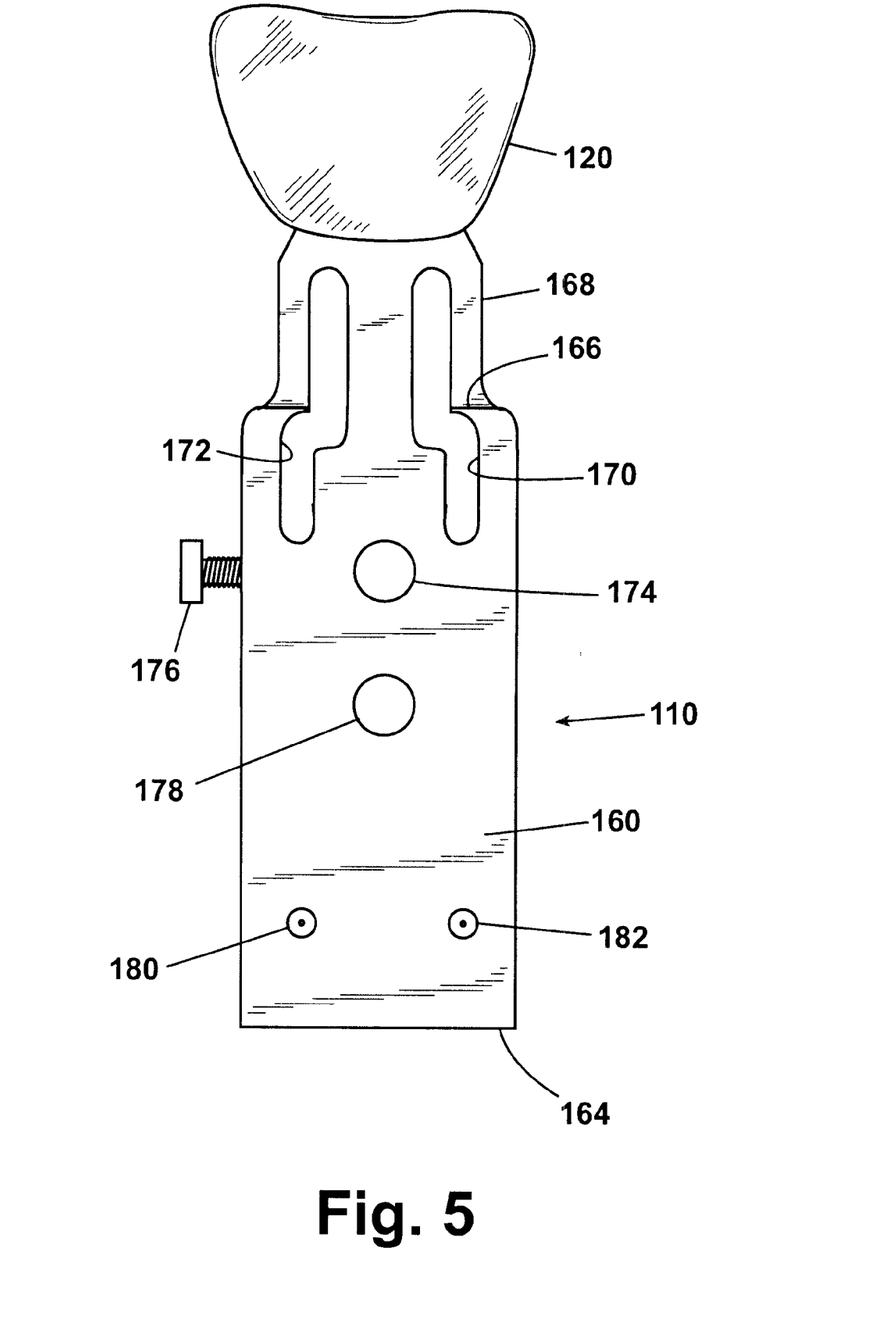
FIG. 5 is superior view of the plate component of the embodiment of FIG. 4.
Figure 6:
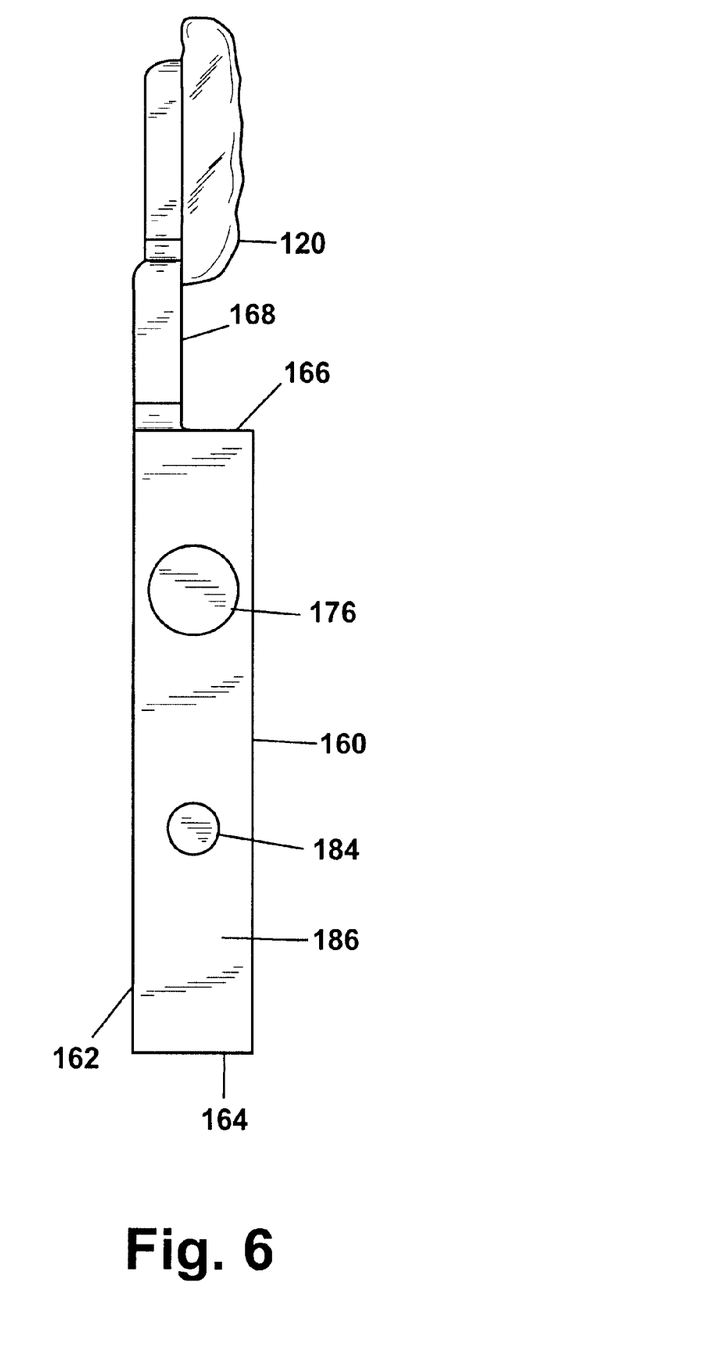
FIG. 6 is a side view of the plate component of FIG. 5.

Referring to FIGS. 5 and 6, the plate 110 and splint 120 of instrument 100 are shown in greater detail. Plate 110 comprises a generally flat, rectangular plate having a top surface 160, a bottom surface 162, a distal end surface 164 and a proximal end surface 166. A tongue 168, of reduced thickness relative to plate 110, extends proximally from proximal end surface 166 and supports splint 120. As preferred, splint 120 is made of acrylic and is custom molded to fit the dentition of the maxillary dental arch of the patient. Splint 120 is rigidly affixed to tongue 168 by screws or other suitable fastening means. A pair of grooves 170 and 172 extend generally longitudinally relative to plate 110 and pass through plate 110 from top surface 160 to bottom surface 162. Grooves 170 and 172 also extend into and pass through tongue 168 in like manner. Grooves 170 and 172 are Z-shaped such that at the distal ends thereof grooves 170 and 172 are spaced farther apart in the medial-lateral direction than at the proximal ends thereof. Grooves 170 and 172 are of sufficient width to permit screws 134 and 144 (as shown in FIG. 4) to pass therethrough. A hole 174 passes through plate 110 from top surface 160 to bottom surface 162 and is sized to receive therein primary lever 150. A setscrew 176 is provided to secure primary lever 150 within hole 174. An alternate hole 178 is provided as an alternate location for primary lever 150. A pair of threaded holes 180 and 182 is provided in top surface 160 for threadedly receiving screws 136 and 146 (as shown in FIG. 4) therein. A hole 184 is provided in side surface 186 of plate 110 for receiving the secondary lever 152 (as shown in FIG. 4) therein.

Figure 7:
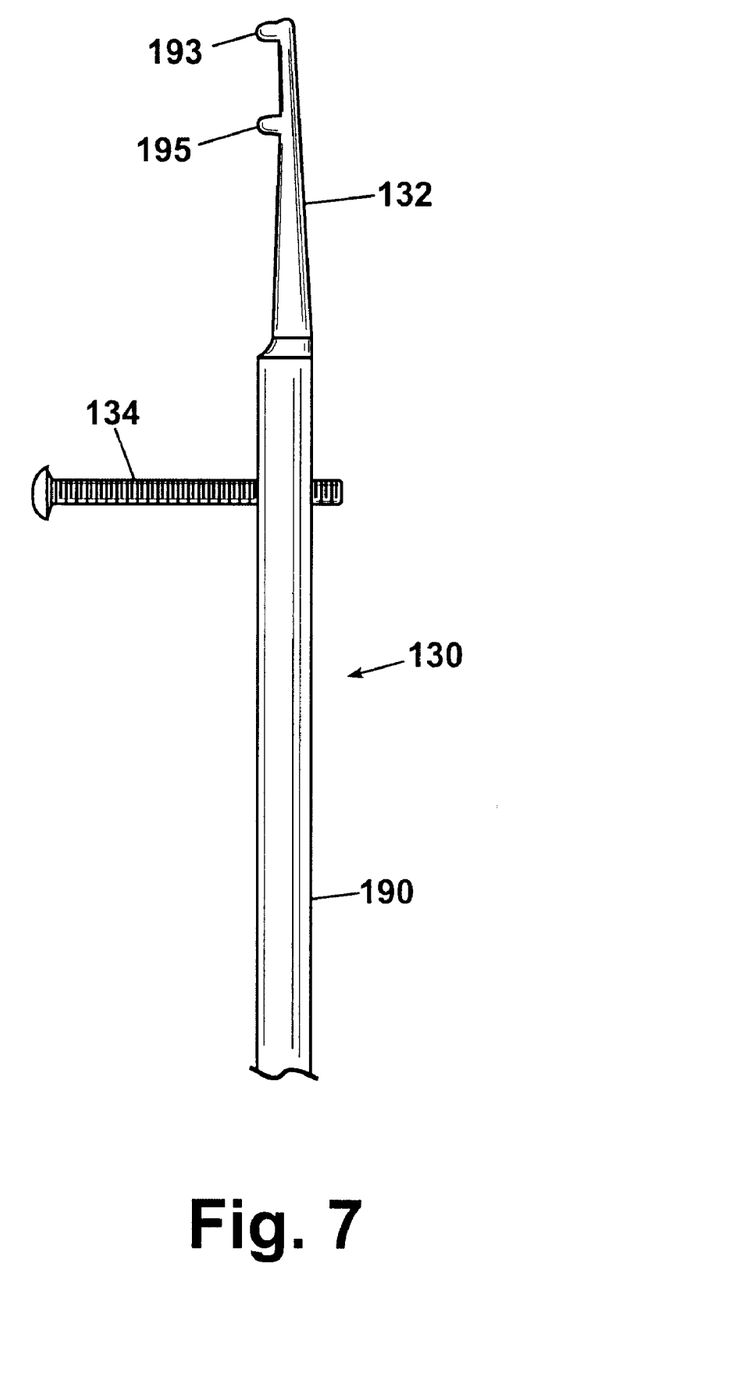
FIG. 7 is a side view of a retention rod of the embodiment of FIG. 4.
Figure 8:
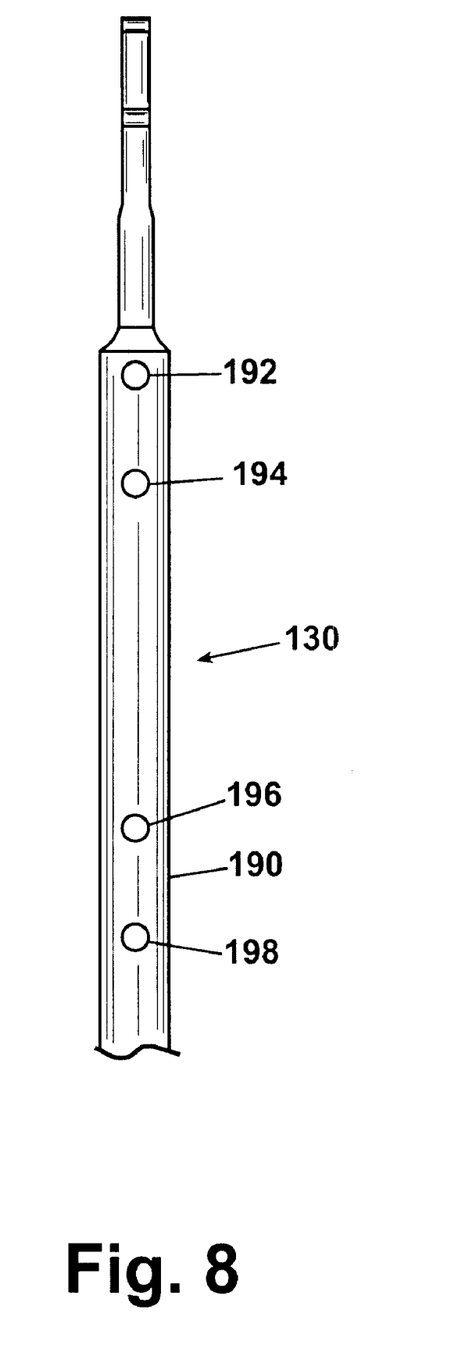
FIG. 8 is an inferior view of the retention rod of FIG. 7.

Referring to FIGS. 7 and 8, retention rod 130 is shown in greater detail. Retention rod 140 is essentially similar. Rod 130 includes a distal body 190 having a plurality of internally threaded alternate holes 192 and 194 for receiving screw 134 therein. Also included are a plurality of internally threaded alternate holes 196 and 198 for receiving screw 136 (as shown in FIG. 4) therein. A tapered nasal extension prong 132 extends proximally from rod 130, and includes a pair of spaced teeth 193 and 195 extending from prong 132 in the inferior direction.

During surgery, the instrument 100 is used as follows. The Le Forte III osteotomies having been performed, but not necessarily completely, the plate 110 and attached splint 120 are inserted into the oral cavity and positioned such that the splint 120 is in intimate engagement with the dentition of the maxilla. Splint 120 will have been custom formed to fit the dentition prior to the surgery. The nasal extension prong 132 of retention rods 130 and 140 are then inserted into the nasal cavity of the Le Forte III fragment, with the teeth 193 and 195 of nasal extension prong 132 engaging the nasal floor. Screws 134 and 144 are then inserted through grooves 172 and 170, respectively, from below, such that the head of screw 134, 144 engages the bottom surface 162 of plate 110. The ends of screws 134, 144 are threaded into one of the available threaded holes 192, 194 of rods 130 and 140. Subsequently, screws 136 and 146 are threaded through one of the available holes 196, 198 of rods 130 and 140 from above, and thence threaded into holes 180 and 182, respectively, of plate 110. Screws 134, 144, 136 and 146 are tightened until nasal extension prongs 132 and 142 are drawn tightly against the nasal floor, and splint 120 is drawn tightly against the dentition. Primary lever 50 is inserted into hole 174 of plate 110 and setscrew 176 is tightened to secure it in place. By pushing with one hand on the forehead of the patient and pulling with the other hand on primary lever 150, the midface fragment is broken free of the skull even without the osteotomies having been complete. Secondary lever 152 can be used to apply torsion if necessary to mobilize the midface fragment.

Although the present invention has been described particularly with regard to preferred embodiments, the scope of the invention is not intended to be limited thereby. The invention in which an exclusive right is claimed is defined by the claims appended below.

I claim:

1. An instrument for mobilizing the midface bones of a human skull having a maxilla including a dental arch, a nasal cavity including a nasal floor, and a forehead, at least a partial osteotomy between the midface bones and the skull having been performed, comprising:

a first member including a dentition engaging portion for engaging the dental arch of the maxilla;

a second member including a nasal engaging portion for engaging the nasal floor of the nasal cavity;

an adjustable member connected to the first member and to the second member and adjustable to draw the first and second members toward each other, whereby the first member can be drawn against the dental arch and the second member can be drawn against the nasal floor; and a lever connected to at least one of the first and second members, disposed anteriorly of the forehead and extending in a superior-inferior direction relative to the skull when the first and second members are engaged with the dental arch and nasal floor, respectively, whereby simultaneously pulling the lever anteriorly and pushing the forehead posteriorly breaks the midface bones free from the skull.

2. The instrument of claim 1, in which the dentition engaging portion includes a splint generally conforming to the dental arch.

3. The instrument of claim 2, in which the splint is custom molded to fit the dentition of the dental arch.

4. The instrument of claim 3, in which the splint is made of acrylic.

5. The instrument of claim 1, in which the nasal engaging portion includes separate portions, each receivable within a respective nostril.

6. The instrument of claim 5, in which the adjustable member includes separately adjustable portions, each connected to a respective one of the separate portions of the nasal engaging portion.

7. The instrument of claim 6, in which each separate portion of the nasal engaging portion includes a nasal extension prong.

8. The instrument of claim 7, in which each nasal extension prong includes at least one tooth extending in the inferior direction when the second member is drawn against the nasal floor.

9. The instrument of claim 5, in which the adjustable member is disposed anteriorly of the maxilla when the first and second members are engaged with the dental arch and nasal floor, respectively.

10. The instrument of claim 9, in which the adjustable member includes a first adjuster disposed proximate a proximal end of the first member and a second adjuster disposed proximate a distal end of the first member, whereby the spacing between the proximal end of the first member and the second member, and between the distal end of the first member and the second member, can be adjusted separately.

11. The instrument of claim 10, in which each separate portion of the nasal engaging portion includes a retention rod.

12. The instrument of claim 11, in which each retention rod includes a nasal extension prong.

13. The instrument of claim 12, in which each nasal extension prong includes at least one tooth extending in the inferior direction when the second member is drawn against the nasal floor.

14. The instrument of claim 11, in which at least one of the first and second adjusters includes separate elements, each separately engaging a respective one of the retention rods.

15. The instrument of claim 14, in which each separate element of at least one of the first and second adjusters includes a threaded screw rod threadedly engaged with a respective one of the retention rods.

16. The instrument of claim 1, and further including a second lever connected to at least one of said first and second members, disposed anteriorly of the maxilla, and extending in a medial-lateral direction relative to the skull when the first and second members are engaged with the dental arch and nasal floor, respectively, whereby moving the lever in a superior-inferior direction relative to the skull imparts torsion to the midface bones to break the midface bones free from the skull.

17. An instrument for mobilizing the midface bones of a human skull, comprising:

a grasping member for grasping the midface bones; and a lever having a first portion connected in cantilever fashion to the grasping member and having a second portion displaced from the grasping member in a superior-inferior direction relative to the skull;

whereby manually displacing the second portion of the lever in an anterior-posterior direction relative to the skull breaks the midface bones free from the skull.

18. The instrument of claim 17, in which the human skull includes a dental arch and the grasping member includes a first member for engaging the dental arch.

19. The instrument of claim 18, in which the human skull includes a nasal cavity and the grasping member includes a second member for engaging the nasal cavity.

20. The instrument of claim 19, and further including an adjustable member connected to the first member and to the second member and adjustable to draw the first and second members toward each other in a superior-inferior direction relative to the skull.

* * * * *

UNITED STATES PATENT AND TRADEMARK OFFICE
CERTIFICATE OF CORRECTION

PATENT NO. : 6,547,796 B1  Page 1 of 1
DATED : April 15, 2003
INVENTOR(S) : Martin Chin It is certified that error appears in the above-identified patent and that said Letters Patent is hereby corrected as shown below:

Column 2,
Line 32, "from" should be -- front --.

Column 3,
Lines 32, 37, 40 and 41 "LeForte" should be -- LeFort --.

Column 5,
Lines 25 and 32 "LeForte" should be -- LeFort --.
Line 37, "screw" should be -- screws --.
Line 48, "lever 50" should be -- lever 150 --.

Signed and Sealed this

Sixteenth Day of December, 2003

JAMES E. ROGAN
*Director of the United States Patent and Trademark Office*